United States Patent
Krever et al.

(10) Patent No.: US 8,197,536 B2
(45) Date of Patent: Jun. 12, 2012

(54) METHOD FOR PLACING A MEDICAL DEVICE AT A BIFURCATED CONDUIT

(75) Inventors: Matthew Krever, Warren, NJ (US); Robert Burgermeister, Bridgewater, NJ (US); Edwin Schulting, VD (NL); Wilhelmus van Erp, KS (NL); Richard Dirks, DC (NL)

(73) Assignee: Cordis Corporation

( * ) Notice: Subject to any disclaimer, the term of this patent is extended or adjusted under 35 U.S.C. 154(b) by 520 days.

(21) Appl. No.: 11/591,396

(22) Filed: Nov. 1, 2006

(65) Prior Publication Data
US 2008/0125847 A1    May 29, 2008

Related U.S. Application Data

(60) Provisional application No. 60/781,461, filed on Mar. 10, 2006.

(51) Int. Cl.
*A61F 2/28* (2006.01)
*A61F 11/00* (2006.01)

(52) U.S. Cl. ...................... 623/1.35; 606/108

(58) Field of Classification Search .................. 623/1.35, 623/1.42, 1.11, 1.15; 606/194, 108; 604/101.01
See application file for complete search history.

(56) References Cited

U.S. PATENT DOCUMENTS

| | | | |
|---|---|---|---|
| 5,669,924 A | 9/1997 | Shaknovich | |
| 6,129,738 A | 10/2000 | Lashinski et al. | |
| 6,193,749 B1 * | 2/2001 | Schroeder et al. | 623/1.42 |
| 6,210,429 B1 | 4/2001 | Vardi et al. | |
| 6,254,593 B1 * | 7/2001 | Wilson | 623/1.11 |
| 6,346,089 B1 | 2/2002 | Dibie | |
| 6,371,978 B1 | 4/2002 | Wilson | |
| 6,475,208 B2 | 11/2002 | Mauch | |
| 6,702,802 B1 | 3/2004 | Hancock et al. | |
| 6,749,628 B1 | 6/2004 | Callol et al. | |
| 6,884,258 B2 * | 4/2005 | Vardi et al. | 623/1.11 |

(Continued)

FOREIGN PATENT DOCUMENTS

WO    WO 00/44307 A1    8/2000

(Continued)

OTHER PUBLICATIONS

Office Action mailed Mar. 24, 2011 in related U.S. Appl. No. 11/591,656.

*Primary Examiner* — Thomas J Sweet
*Assistant Examiner* — Jason-Dennis Stewart

(57) ABSTRACT

A method for treating a diseased body conduit at a bifurcation point is provided. A system having devices mounted thereon is advanced into the bifurcated region of the conduit. The system includes a delivery means, such as a catheter having a shaft with varying torsional properties along its length and a delivery apparatus mounted at its distal end. A distal end of the delivery means can be inserted into the main branch and at least one side branch of a vessel bifurcation. The distal end includes at least two expansion members having expandable devices or prostheses mounted thereon. One device is configured such that one expansion member extends through the length of the scaffold while the other expansion member extends through the side-structure of the scaffold. A second scaffold is mounted on the expansion member extending through the side-structure of the first scaffold. The devices are positioned within the main and side branches of the bifurcation and are expanded.

51 Claims, 16 Drawing Sheets

U.S. PATENT DOCUMENTS

| | | | |
|---|---|---|---|
| 6,962,602 B2 * | 11/2005 | Vardi et al. | 623/1.11 |
| 2001/0003161 A1 | 6/2001 | Vardi et al. | |
| 2001/0016756 A1 | 8/2001 | Blach et al. | |
| 2001/0037138 A1 | 11/2001 | Wilson et al. | |
| 2002/0077591 A1 | 6/2002 | Happ et al. | |
| 2003/0068355 A1 * | 4/2003 | Shanley et al. | 424/426 |
| 2003/0074047 A1 * | 4/2003 | Richter | 623/1.11 |
| 2003/0125802 A1 * | 7/2003 | Callol et al. | 623/1.35 |
| 2004/0098114 A1 * | 5/2004 | Wilson et al. | 623/1.35 |
| 2004/0220606 A1 | 11/2004 | Goshgarian | |
| 2004/0220660 A1 * | 11/2004 | Shanley et al. | 623/1.16 |
| 2004/0249441 A1 * | 12/2004 | Miller et al. | 623/1.15 |
| 2005/0060027 A1 * | 3/2005 | Khenansho et al. | 623/1.35 |
| 2005/0119731 A1 | 6/2005 | Brucker et al. | |
| 2005/0131532 A1 * | 6/2005 | Sirhan et al. | 623/1.42 |
| 2005/0171598 A1 * | 8/2005 | Schaeffer | 623/1.35 |
| 2005/0177118 A1 * | 8/2005 | Hoganson et al. | 604/288.01 |
| 2006/0036315 A1 * | 2/2006 | Yadin et al. | 623/1.35 |
| 2006/0085061 A1 * | 4/2006 | Vardi et al. | 623/1.35 |
| 2006/0100578 A1 | 5/2006 | Lieberman | |
| 2006/0206188 A1 | 9/2006 | Weber et al. | |

FOREIGN PATENT DOCUMENTS

| | | |
|---|---|---|
| WO | WO 0044307 A1 | 8/2000 |

* cited by examiner

METHOD FOR PLACING A MEDICAL DEVICE AT A BIFURCATED CONDUIT

CROSS REFERENCE TO RELATED APPLICATIONS

This application claims priority from U.S. Provisional Patent Application Ser. No. 60/781,461 filed on Mar. 10, 2006, titled Apparatus for Scafolding a Bifurcated Conduit and commonly assigned with the present invention.

FIELD OF THE INVENTION

This invention generally relates to devices that are used to treat disease states of the human vasculature. In particular, this invention relates to a device used to treat disease states in a bifurcating region of a body lumen such as a coronary artery or a billiary duct.

BACKGROUND OF THE INVENTION

In the human body there are numerous conduits, for example blood vessels and ducts that carry necessary fluids to internal organs or allow for the excretion of those fluids. These conduits can become diseased or clogged causing severe, adverse consequences. One example of a disease afflicting a body conduit is arteriosclerosis, caused by the presence of matter on or in the inner wall of blood vessels resulting in occlusion of the vessel. One possible treatment for arteriosclerosis is Percutaneous Transluminal Coronary Angioplasty (PTCA), which often is accompanied by the placement of a device, such as a stent.

Arteriosclerosis and related diseases can occur throughout the vascular system. One such location is a bifurcation, which is a point where a vessel divides into two separate conduits. It is difficult to place a device in a bifurcation since the vessel bifurcations generally have circumferential asymmetry requiring the device to be precisely positioned, provide adequate coverage of the diseased area, provide access to any diseased area located distal to the bifurcation, and maintain vessel patency in order to allow adequate blood flow. Therefore, the stent must provide adequate coverage to the diseased portion of the bifurcated vessel, without compromising blood flow, and extend to a point within or beyond the diseased portion.

Conventional stents are designed to repair areas of blood vessels that are removed from bifurcations. For example, conventional stents are normally deployed such that the entire stent is either in the parent vessel or the proximal portion of the stent is in the parent vessel and the distal portion is located in the side branch vessel. In either case, either the side branch vessel or the parent vessel could become partially blocked by the stent struts. One vessel is repaired at the site of the bifurcation at the expense of obstruction of the alternate vessel. Blood flow would be compromised into one of the vessels as well as access for future treatment. Alternatively, if the obstruction of blood flow is to be avoided using conventional stents, they must be positioned in such a manner as to leave areas of the bifurcation untreated.

In order to overcome the limitations of conventional stents, branched stents have been employed. Branched stents generally comprise a main section and one or more branch sections that are inserted into the main and branch vessel(s). Some designs for branched stents feature a single piece or unibody device that is pre-shaped to roughly match the contours of the bifurcation. Because of their shape, unibody devices are difficult to deliver through a small diameter sheath or catheter to the bifurcation site. Another delivery problem experienced with unibody designs is wrapping of the wire and device due to the contortions experienced during delivery. Finally, unibody designs are difficult to manufacture as most stents are constructed from a single tube or sheet of material. In effect, two stents would need to be formed and connected together. A unibody device is also difficult to coat with substances such as drugs or other therapeutic agents that are useful in preventing restenosis.

U.S. Pat. No. 6,210,429—Vardi discloses a branched stent device that is formed using at least two conventional stents. As shown in Vardi, a first stent is positioned and expanded in the main branch vessel. The first or main branch stent includes a side opening or port that apposes the side branch vessel opening. A second stent can be placed through the side opening of the main branch stent into the side branch vessel where it is expanded. The two stents can overlap or the side branch stent can be connected to the main branch stent by tabs. A drawback to this approach is that it requires multiple steps to place the branched stent within the bifurcation. For example, the physician must align the opening of the main branch stent with the ostium of the side branch vessel. Only then can the second stent be placed in the side branch. If the second or side branch stent is not accurately positioned and contacts the main branch stent, the opening of the main branch stent may become compromised.

Another branch stent design is disclosed in U.S. Pat. No. 6,749,628—Callol. The side branch stent comprises a proximal, middle and distal section. The middle section includes a "trap door" that protrudes into the ostium of the branch vessel when the stent is expanded. The stent is mounted at the distal end of the delivery catheter assembly. In particular a first, long balloon extends through the proximal, middle and distal sections of the stent. A second, shorter balloon extends from the proximal section of the stent and protrudes through the trap door. Guidewires extend through each of the balloons such that the stent is positioned against the carina of the bifurcation. The balloons are then inflated causing the stent to expand and be fixed in the main branch and extend, via the trap door, into the side branch vessel. A second stent can then be inserted into the side branch vessel.

It is desired to simultaneously place the sections of the branched stent in the main and branch vessels. The delivery catheter system of Callol fails to disclose a method for accomplishing this. Moreover, Callol places two wires or wire-like elements in each branch to orient the device to match the vessel anatomy. The shortcoming of this approach is twofold. First, by requiring delivery of the medical device to the location of the bifurcation over two wires for substantially the entire delivery, the chance that the devices and/or wires will wrap is greatly increased. This prevents complete delivery of the devices and can result in the clinician having to withdraw a wire and rewire the vessel. Secondly, solely relying on two wires for orientation is insufficient to guarantee full and proper alignment of the entire medical apparatus with the side branch ostium.

U.S. Pat. No. 6,884,258—Vardi discloses a method for advancing and deploying a bifurcated system with the use of three guide wires. A first wire is placed in the main vessel beyond the bifurcation site while a second wire is placed into a branch vessel. A catheter is placed over the main guidewire to a position near the bifurcation. The catheter includes a side sheath that protrudes from the distal end of the catheter. A third wire is advanced through a side sheath into the branch vessel. Thereafter, the first wire is withdrawn as is the catheter leaving the main and branch guidewires in place. While this method ensures that guide wires are accurately placed in the main vessel and branch vessel, it is still only useful for placing a single stent to treat the main vessel. For example, the problems associated with wire wrapping are still present.

Currently, there is no apparatus, delivery system or method that can simultaneously place separate stents in a vessel bifurcation. The present invention is designed to address this need.

SUMMARY OF THE INVENTION

According to the invention, a system for treating a bifurcation that is readily deliverable into a region of a body conduit having typically asymmetric anatomy, such as a vessel bifurcation is provided. The system comprises a catheter having a shaft with varying torsional properties along its length and a delivery apparatus mounted at its distal end. A device that can be inserted into the main branch and at least one side branch of a vessel bifurcation is mounted on the delivery apparatus.

The catheter generally comprises a long thin hypotube shaft with varying torsional properties along its length. The proximal portion of the shaft includes an adapter having multiple ports. Some ports are in fluid communication with an inflation lumen while another port is in communication with an over-the-wire (OTW) guidewire lumen. A mid-portion of the shaft includes at least one rapid exchange (Rx) guidewire port in communication with a Rx guidewire lumen. In addition, the mid-portion includes an inflation lumen in communication with the inflation lumen of the proximal portion and, in certain embodiments, at least one over-the-wire (OTW) guidewire lumen in communication with the OTW lumen of the proximal portion of the shaft.

A distal portion of the catheter shaft splits into two expansion members each containing a guidewire lumen and an inflation lumen. The guidewire lumens are in communication with the Rx lumens of the mid-portion. Alternatively, at least one guidewire lumen may be in communication with the OTW lumen of the mid-portion and proximal portion. The distal portion of the catheter includes an inflation lumen in fluid communication with the inflation lumen of the proximal portion and mid-portion. In one embodiment, the inflation lumen splits at its distal end to communicate with each expansion member and provide for simultaneous expansion. Alternatively, two inflation lumens are provided along the length of the catheter device allowing for communication with multiple inflation devices providing for independent expansion of the members.

It is desirable to have the proximal portions of the shaft be flexible enough to allow for navigation through a body conduit but rigid enough to prevent kinking. In contrast, the distal portion of the shaft proximal to the delivery apparatus (e.g. stents) is significantly more flexible and torsionally compliant than sections proximal thereto in order to allow rotation of the distal portion of the shaft to align with the branch vessel(s) as well as enhance deliverability. For example, as the distal end is advanced over the guide wires, it will follow the wires, which have been advanced into the main and side branches, to obtain proper orientation. In order to minimize the effects due to the differing torsional properties of the distal and proximal portions of the shaft, a torsional transfer section is included. This section torsionally separates the two portions of the shaft through it's increased torsional compliancy and absorbs possible torque from the proximal end isolating it from transfer to the distal portion.

The expansion members may comprise at least two balloons located at the distal ends of the distal portions of the catheter. A first balloon is configured to extend into a side branch vessel and is generally shorter than a second balloon. Varying the length of the two balloons optimizes cooperation between the balloons by minimizing overlap to match bifurcation anatomy. Alternatively, at least one of the two balloons may be utilized that has stepped expansion diameters along its length such that one portion of the balloon has a smaller expansion diameter proximally than distally. This also helps to better match bifurcation anatomy if two similar length balloons are used.

A first and second stent are mounted on the ends of the catheters. The first and second stent generally comprise a series of struts that are joined together by round joints to form hoops or elements. Adjacent hoops or elements are joined together by a plurality of bridges. The bridges are shaped to allow for the stent to flex in a longitudinal (?) direction. The round joints join the struts together in a manner that allows the stent to assume a first, smaller diameter and a second, larger diameter.

The first stent is mounted on the two balloons such that the second balloon extends through the length of the stent. The first stent is modified such that the first balloon can extend through the struts of the stent. This can be accomplished by removing a bridge, varying the spacing or number of the struts or any other modification that permits passage of the first balloon there through. A second stent is mounted on the distal end of the first balloon and aligned with the distal end thereof. The second stent is not connected to the first stent and is generally shorter with a smaller or equal expansion diameter.

A distal torque transmission element is positioned between the first stent and the second stent. This element mitigates device wrapping caused by the transmission of rotation from the more flexible distal leg portion of the stents to the more rigid proximal portion of the first stent. Without this element, rotational "kinking" of the stents can occur due to the rapid transition in torsional stiffness of the device. In one embodiment of the invention, the distal portion of the side branch is coupled to the proximal end of main branch. This may be accomplished by a wire, coil, tube or the like that joins the two balloon/stent components. Alternatively, the stent can include a temporary mechanical connection, i.e. a strut or tab

BRIEF DESCRIPTION OF THE DRAWINGS

The features and advantages of the invention will be apparent to those of ordinary skill in the art from the following detailed description of which.

DETAILED DESCRIPTION OF THE PREFERRED EMBODIMENTS

Figure 1A:
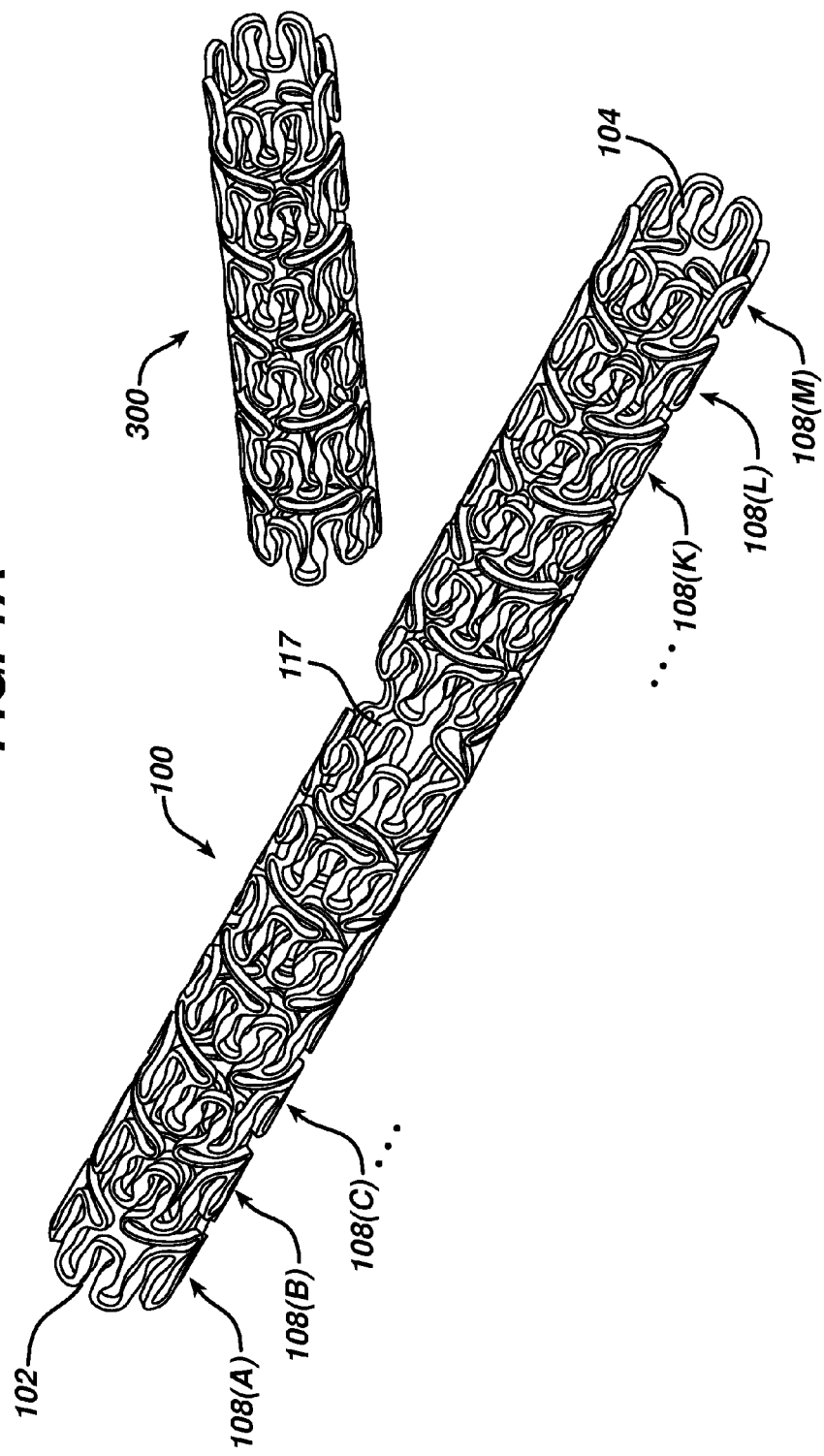
FIG. 1A is a perspective view of a pair of stents for use in a vessel bifurcation

An apparatus, system and method for treating a diseased conduit of a human body at a bifurcation will be described with reference to the FIG. 1A shows a first stent 100 and a second stent 300 that may be placed within a conduit, for example at a vessel bifurcation. Although FIG. 1A shows stent 100 and 300 to be substantially similar, it is important to note that each of stents 100 and 300 may have different characteristics. For example, stents 100 and 300 may be constructed from different materials, have different geometries and/or be coated with or have different agents embedded therein. In particular, stent 100 may be a bare metal stent while stent 300 is a polymeric stent coated with a therapeutic agent or having the therapeutic agent embedded in its polymer matrix. Additionally, stent 100 may be coated with a therapeutic agent, but have a wider diameter or geometry, the characteristics of which are discussed in greater detail below, than stent 300.

Figure 1B:
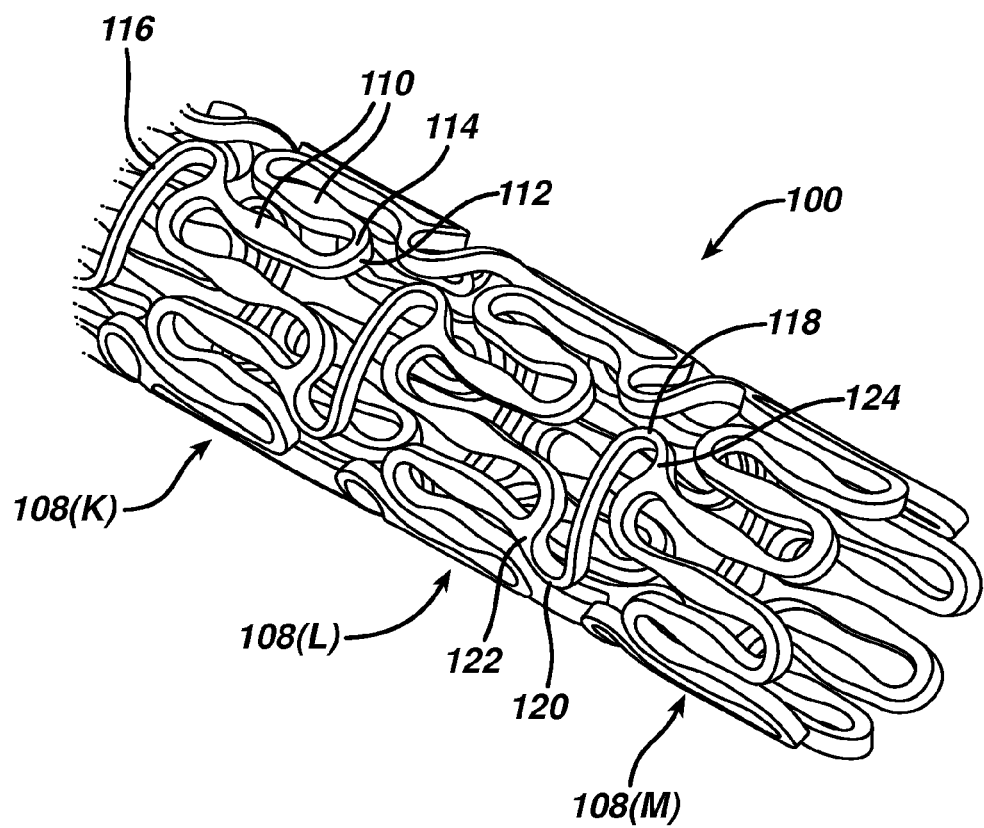
FIG. 1B is a perspective view of the end of the stents shown in FIG. 1A.
Figure 2:
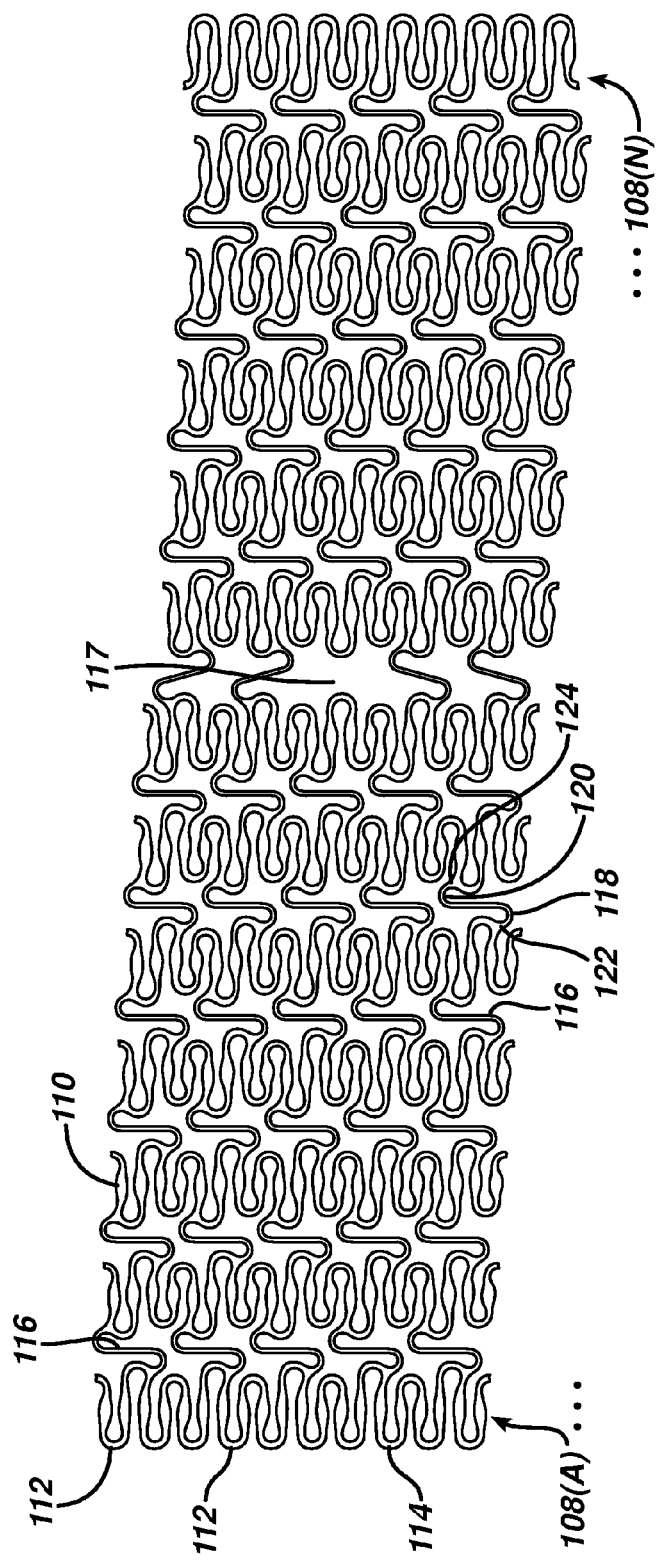
FIG. 2 is a sectional, flat view of the longer stent shown in FIG. 1A.

For ease of description, the general geometry and characteristics of a stent will be described with reference to stent 100 as shown in FIGS. 1-2. The stent 100 is employed in connection with the present invention and is a generally tubular member having proximal and distal open ends 102 and 104. The tubular member has a first small diameter for insertion into a patient and navigation through the vessels, and a second larger diameter for deployment in the target area of the body conduit. The tubular member is made from a plurality of adjacent hoops 108, FIGS. 1-2 showing hoops 108(a)-108(m), extending between the front and back ends 102 and 104. It will be appreciated by one of ordinary skill in the art that the number of hoops 108 may be increased or decreased to vary the length of the stent 100. The hoops 108 include a plurality of longitudinal struts 110, wherein adjacent struts are connected at opposite ends by loops 112. The loops 112 are generally curved and semi-circular.

The stent further includes a plurality of bridges 116 which connect adjacent hoops 108. Each bridge 116 has two ends 118 and 120. The bridges 116 have one end attached to one strut and/or loop, and another end attached to a strut and/or loop on an adjacent hoop. The bridges 116 connect adjacent struts together at bridge to loop connection points 122 and 124. For example, bridge end 118 is connected to loop 114(a) at bridge to loop connection point 124. Each bridge to loop connection point has a center. The bridge to loop connection point is separated angularly with respect to the longitudinal axis. That is, the connection points are not immediately opposite each other. Essentially, one could not draw a straight line between the connection points, wherein such line would be parallel to the longitudinal axis of the stent.

The above-described geometry helps to better distribute strain throughout the stent, prevents stent component to stent component contact when the stent is bent, and minimizes the opening size between the struts 110, loops 112 and bridges 116. Thus, the number and nature of the design of the struts 110, loops 112, and bridges 116 can be varied to provide for optimal spacing between the struts, loops and bridges. For example, as shown in FIG. 2, a bridge 116 has been removed in region 117 of the stent 100. In its unexpanded and expanded state, region 117 provides an optimal space through which a balloon or other expansion device may be extended as is described in greater detail below. Of course, region 117 need not be located at the axial center of the stent. It may be offset to either the proximal or distal end of stent 100. Alternatively, fewer struts may be employed such that larger openings exist between each strut also permitting an expansion member. Yet another alternative requiring is to manually deform a section along the stent 100 to create a space through which a balloon may be extended.

The components of stent 100 and 300, i.e., the struts 110, loops 112 and flexible links 116, may all, or separately, be coated with a therapeutic or otherwise beneficial substance, such as radiopacifying agents like tantalum. For example, the components may have drug coatings or drug and polymer coating combinations that are used to deliver drugs, i.e. therapeutic and/or pharmaceutical agents including: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP)II$_b$III$_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); antiinflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF) platelet derived growth factor (PDGF), erythropoetin; angiotensin receptor blocker; nitric oxide donors; anti-sense oligionucleotides and combinations thereof; cell cycle inhibitors, mTOR inhibitors, and growth factor signal transduction kinase inhibitors.

It is important to note that one or more of the lattice components (e.g. hoops, loops, struts and flexible links) are coated with one or more of the drug coatings or drug and polymer coating combinations. Additionally, as mentioned above, the stents 100 and/or 300 can alternatively be constructed from a polymer material such as a biodegradable material capable of containing and eluting one or more drugs, in any combination, in accordance with a specific or desired drug release profile.

FIGS. 3-7 illustrate a delivery apparatus for devices such as stents 100 and 300 described above. As shown in FIGS. 5A-C the stent delivery apparatus 10 generally comprises a shaft 14, which may be encased in a biocompatible sheath, is shown in greater detail in FIGS. 5C and 5D. The shaft 14 has a proximal portion 18 and near distal portion 19, which will be described in greater detail below. The proximal 18 and near distal portion 19 of the shaft are made from a relatively stiff material such as stainless steel, Nitinol, or any other suitable material, and the distal portion may be made from a polyethylene, polyimide, Pellethane, Pebax, Vestamid, Cristamid, Grillamid or any other suitable material. If utilized, the sheath may comprise a polymeric material and has a proximal end terminating at sheath hub 40. At least one marker 34 is disposed along the outer surface of the sheath of shaft 14.

Figure 5A:
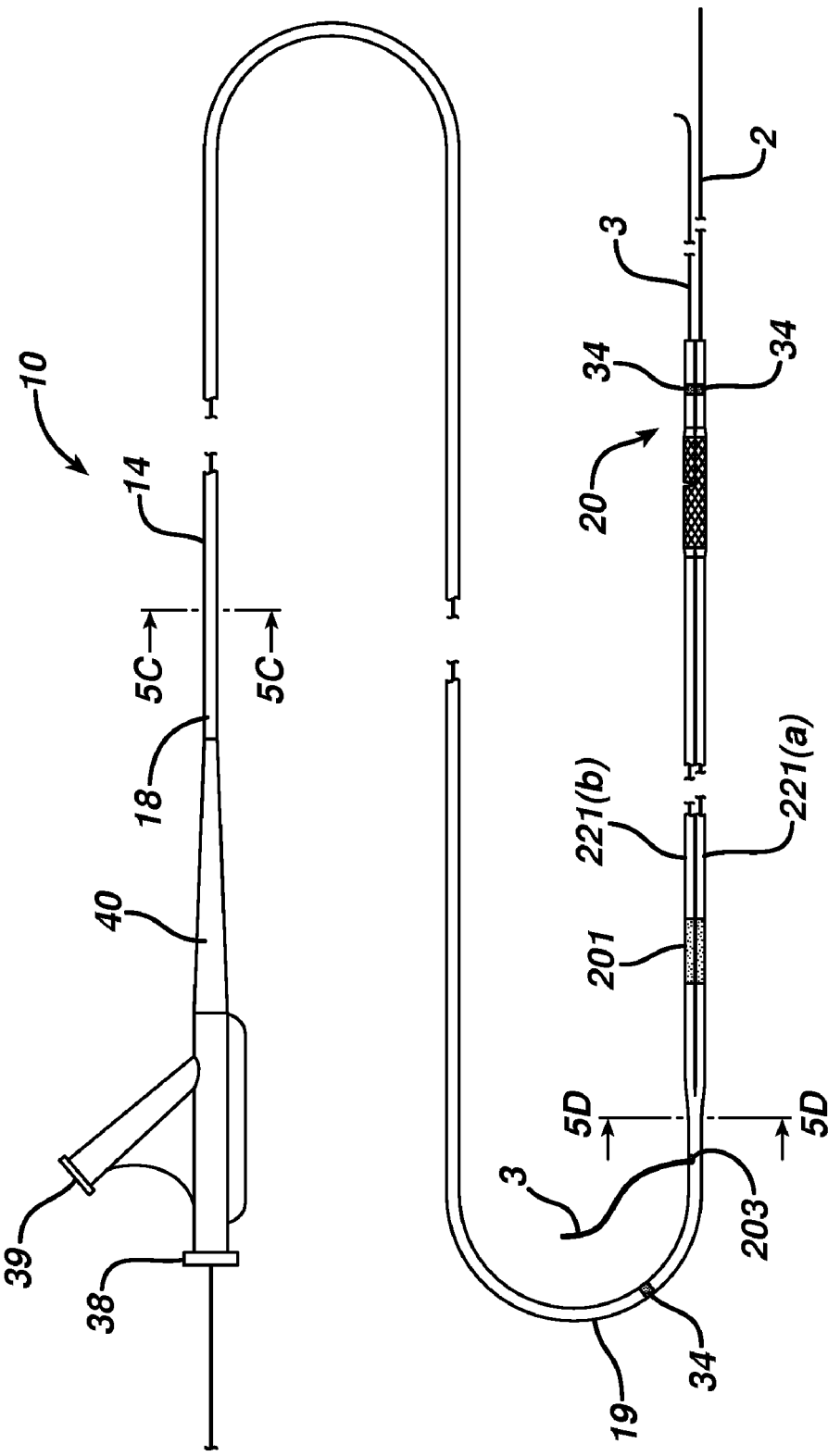
FIG. 5A is a side view of the delivery system for placing the stents of FIG. 1A at a vessel bifurcation.

The proximal portion 18 includes an adapter 38, such as a Tuohy Borst Valve having at least one port 39. The port 39 is in fluid communication with an inflation lumen 11, shown in greater detail in FIG. 5C, while another port is in communication with an over-the-wire (OTW) guidewire lumen 202. In an alternate embodiment adapter 38 includes another port in communication with a second inflation lumen. As shown in FIG. 5A, the near distal portion 19 includes at least one rapid exchange (Rx) guidewire port 203 in communication with Rx guidewire lumen 204, shown in detail in FIG. 5D. Near distal portion 19 also includes inflation lumen 11. In yet another alternate embodiment of the invention, the near distal portion 19 includes two Rx ports in communication with guidewire lumens 202 or 204 and replaces OTW guidewire lumen originating at adapter 38. In yet another alternate embodiment of the invention three guidewire lumens are included wherein each lumen can serve as an OTW or Rx lumen or any combination thereof.

Figure 5B:
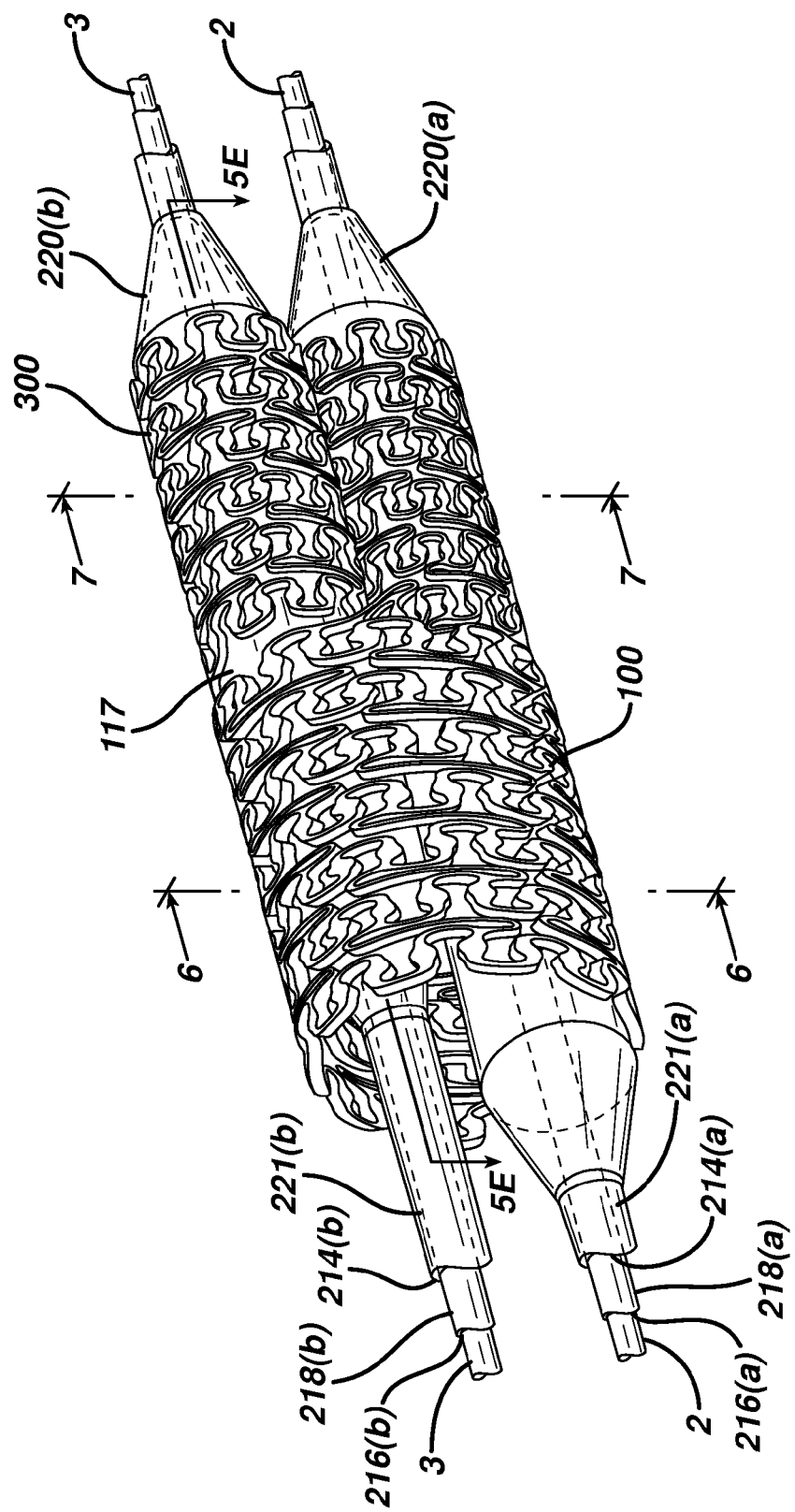
FIG. 5B is a perspective view of showing the stents of FIG. 1A mounted onto the expansion members of the delivery system.
Figure 5C:
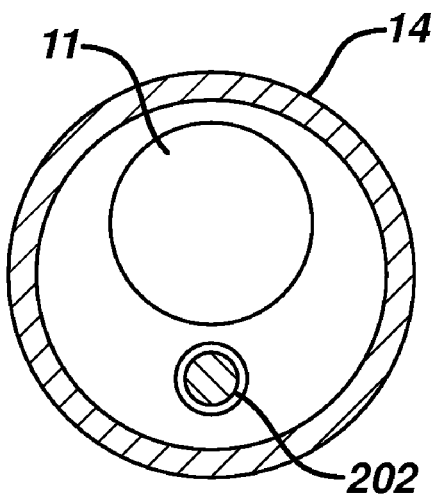
FIG. 5C is a cutaway view taken along line 5C-5C of FIG. 5A.
Figure 5D:
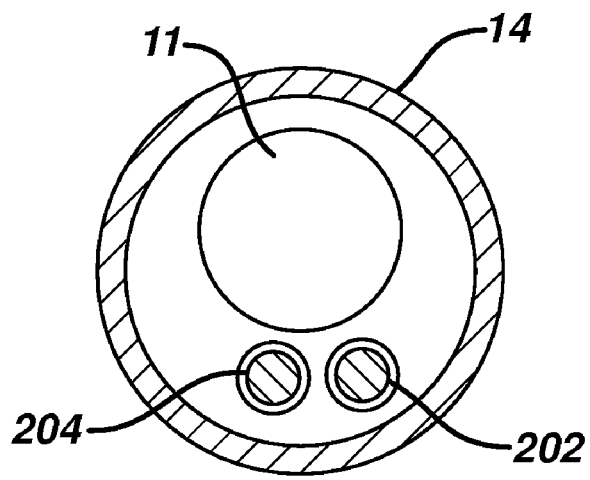
FIG. 5D is a cutaway view taken along line 5D-5D of FIG. 5A.
Figure 6:
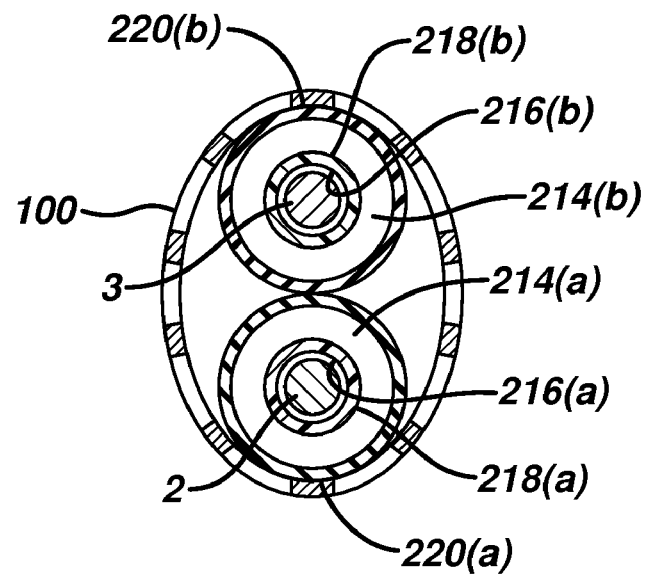
FIG. 6 is a cutaway view taken along line 6-6 of FIG. 5B.

As shown in FIGS. 3 and 5A-B and 6 near distal portion 19 of the catheter shaft 14 is connected to two outer bodies 221(a) and 221(b) having expansion members 220(a) and 220(b) mounted thereon. Outer bodies 221(a) and 221(b) extend proximally from the members 220(a)(b) and enclose shafts 218(a)-(b). As shown in FIG. 6, the shafts 218(a)-(b) contain guidewire lumens 216(a) and 216(b) and define inflation lumens 214(a) and 214(b) between outer bodies 221(a)-(b) and shafts 218(a)-(b). The guidewire lumens 216(a) and 216(b) are in communication with the lumens 202 and 204. For example, one guidewire lumen 216(a) or 216(b) may be in communication with an OTW lumen 202 while another is in communication with lumen 204. The inflation lumens 214(a)-(b) are in communication with the inflation lumen 11. In one embodiment, the inflation lumen 11 communicates with each inflation lumen 214(a)-(b) and provides for inflation of members 220(a)-(b). In an alternate embodiment, not shown in the drawings, two inflation lumens are provided in shaft 14 wherein each separately communicates with lumens 214(a)-(b). This arrangement allows separate inflation of expansion members 220(a) and 220(b).

The proximal 18 and distal portion 19 of the shaft should be flexible enough to allow for navigation through a body conduit but rigid enough to prevent buckling. In contrast, the two shafts 218(a)-(b) and outer bodies 221(a)-(b) are more torsionally compliant than sections proximal thereto in order to allow rotation of the shafts to align with the branch vessel(s) and enhance deliverability. For example, as the distal end 20 of the shafts 218(a)-(b) is advanced over the guide wires 2, 3, it will follow the wires, which have been advanced into the main and side branches (See FIGS. 11-12), to obtain proper orientation.

In order to minimize the effects due to the differing torsional properties of the distal tips 210(a)-(b) and proximal/mid portions 18, 19 of the shaft 14, a torsional transfer section 201 is located proximal to the expansion members 220(a) and 220(b). This section separates and torsionally de-couples portions 18 and 19 from shafts 218(a) and 218(b) and absorbs torque from the proximal and mid portions 18, 19 preventing its transfer to the distal end 20 while allowing the torque transmitted by the distal wires to rotate the distal portion 20 of the delivery system and stents 100 and 300 into proper alignment with the bifurcation. The torsional transfer section may comprise a spring, an elastic material disposed between the sections, a shock absorber, or a kink or other mechanical deformation of the shaft 14. In specific arrangement, the transfer section 201, adjacent the distal end 19 of shaft 14 are constructed of a material that exhibits sufficiently high torsional flexibility so that the distal end 20 of the shafts 218(a)-(b) is able to undergo the rotation necessary to orient the device. Employing an elastomeric material to construct the shafts and/or the bodies 221(a)-(b) is one way to attain this result. In other arrangements, dimensions of shafts 218(a)-(b) and/or bodies 221(a)-(b) can be varied in order to impart torsional flexibility. For example, the wall thickness of shafts 218(a) and/or 218(b) can be reduced or alternatively, the diameter of one or both of the shafts 218(a)-218(b) can be reduced.

As described above, the purpose of the delivery system 10 is to deliver and orient a medical device such as stents 100 and 300 to the target location in a vessel. Although stents 100 and 200 have been described as the medical devices to be oriented in a particular manner at a vessel bifurcation for the purpose of example. However, one of skill in the art would understand that other medical devices that can be incorporated into the distal end of the delivery catheter can also be delivered and oriented, including but not limited to medical balloons, cameras, sensors, drug delivery devices, and various lumens.

One key concept of the present invention is the inducement of a preferential bend along the distal region 20 of the delivery system 10. The preferential bend may be made at any time during the delivery process, but is preferably done prior to advancement of the system to position the stents 100 and 200 to the bifurcation. Accordingly, the delivery system 10 may include an element capable of inducing a preferential bend along the distal end portion of the delivery device to assist in controlling the orientation of the delivery device. The elements may be active component elements or inactive component elements.

Active components include components that can be shaped into a "preferential bend" after introduction into the vasculature. That is to say, they can enter the vasculature having a relatively straight longitudinal configuration and be bent into the desired shape at a subsequent time, preferably once the device reaches the desired location. There are several methods that can be employed to actively induce the preferential bend along the distal region 20 of the delivery system 10 and are presented here for the purpose of example. One of skill in the art would understand that other methods might also be employed.

One method that can be used to induce a preferential bend utilizes hydraulics and a pressure chamber that assumes a curved shape when filled. For example a curved or "banana" shaped medical balloon may be incorporated into the distal end of the delivery member. During delivery the balloon remains relatively straight and flexible in an un-inflated, constrained and wrapped configuration. To impart the preferential bend, a fluid is introduced into the balloon through the delivery catheter, increasing the balloon's internal pressure and ultimately filling the balloon until the balloon assumes is curved shape. The inflated balloon is strong and rigid enough to deflect the distal end of the delivery device into the desired preferential bend. The fluid may be compressible or incompressible, but is preferably a substantially incompressible biologically compatible fluid such as saline.

In another embodiment of the invention, the distal region 20 of the delivery system 10 member includes at least one element that is capable of changing shape upon the introduction of some type of energy. This energy source may come in the form of mechanical, electrical, chemical, thermal or magnetic energy. For example, one embodiment of the invention has at least one mechanical element that changes shape through the application of relative motion or force. These elements may include wires, deflectable tubes, deflectable catheters, or deflectable tip guidewires (for example the Cordis Steer-It™ guidewire). The deflectable elements are located along the distal end of the delivery catheter, and remain relatively straight and flexible when introduced into the vasculature and advance to the desired location. When the clinician desires to induce the preferential bend he imparts mechanical force or motion to the proximal end of the delivery device, which translates this energy into motion along the deflectable distal end portion. This deflection bends the distal end of the delivery device to assume the preferred bend.

In another embodiment of the invention, the delivery system 10 has at least at least one element that changes shape corresponding to a change in electrical potential or current. Elements that change shape under these conditions are known in the art, and include piezoelectrics, bimetallic strips, resistive elements and MEMS (electro-mechanical actuator) devices. When the clinician desires to induce the preferential bend he allows electrical energy to flow to the electrical element. This change is electrical potential or current causes the electrical element to change shape or deflect, bending the deflectable distal end portion. This deflection bends the distal end of the delivery device to assume the preferred bend.

In still another embodiment of the invention, the delivery system 10 has at least one element that changes shape corresponding to a change in a magnetic field. The magnetic field may be internal to the body or vasculature, or external. One particular type of material for this type of application is a magnetostrictive material. Magnetostriction is the changing of a material's physical dimensions in response to changing its magnetization. In other words, a magnetostrictive material will convert magnetic energy into kinetic energy and change shape when it is subjected to a magnetic field. One brand name of a magnetostrictive material is Terfenol™ When the clinician desires to induce the preferential bend he subjects the magnetostrictive element to a magnetic field. This magnetic field causes the magnetostrictive element to convert the magnetic energy to kinetic energy and change shape, bending the deflectable distal end portion. This deflection bends the distal region 20 of the delivery system 10 to assume the preferred bend.

In other embodiments, the delivery system 10 has ferrous or ferromagnetic distal end and respond to an external magnetic field. Accordingly, the distal end of the delivery device may bend toward the attractive magnetic field, or bend away from a repulsive magnetic field, causing a similar bend in the deliver system.

The delivery system 10 may also be actively bent by forces exerted by a chemically responsive element that changes shape corresponding to a change in local chemistry. This change may be caused by a chemical reaction or change in chemical concentration of the element. In either case the chemically responsive element may swell or change stiffness in response to the change in local chemistry.

Similarly, forces exerted by a thermally responsive element may also actively manipulate the delivery system 10. In these embodiments, the change in local temperature may be a result of placing the device into a warm vessel, or alternatively, changing the local temperature by introducing a hot or cold medium. In one embodiment, a thermally responsive element may change shape corresponding to a change in temperature. For example, the material may undergo a change in stiffness, shape or mechanical property as a result in the increase or decrease in local temperature.

In another embodiment the thermally responsive element has components with different coefficients of thermal expansion—for example a bimetallic strip. When the element is introduced into various thermal environments, the different components respond differently, and expand at different rates. This will cause to thermally responsive element to change shape or bend. This deflection bends the distal end of the delivery device to assume the preferred bend. Thermally responsive elements may also undergo a phase change, causing the material to exhibit shape memory or super elastic characteristics. One such material is Nitinol.

Nitinol is utilized in a wide variety of applications, including medical device applications as described above. Nitinol or NiTi alloys are widely utilized in the fabrication or construction of medical devices for a number of reasons, including its biomechanical compatibility, its biocompatibility, its fatigue resistance, its kink resistance, its uniform plastic deformation, its magnetic resonance imaging compatibility, its ability to exert constant and gentle outward pressure, its dynamic interference, its thermal deployment capability, its elastic deployment capability, its hysteresis characteristics, and is moderately radiopaque.

Figure 3:
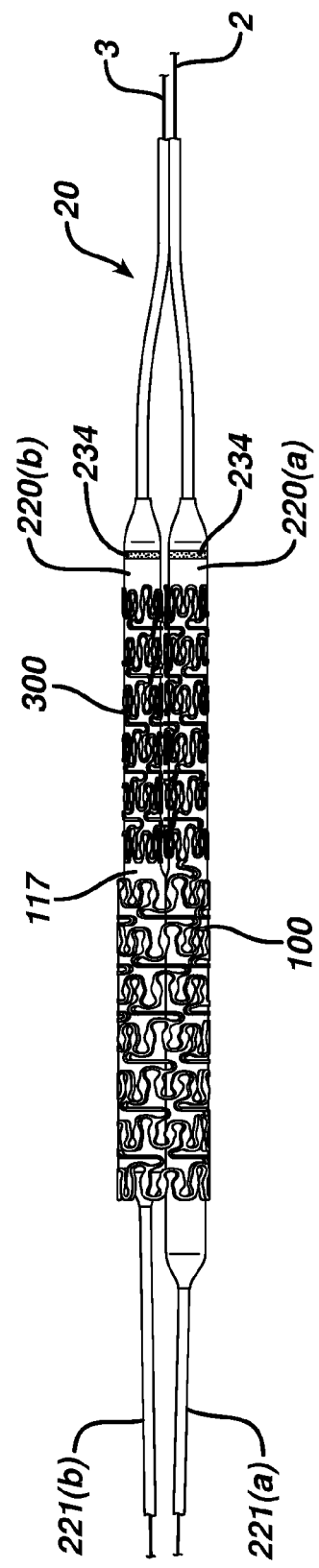
FIG. 3 is a side view showing the stents of FIG. 1A mounted onto expansion members of a delivery system for the stents.
Figure 7:
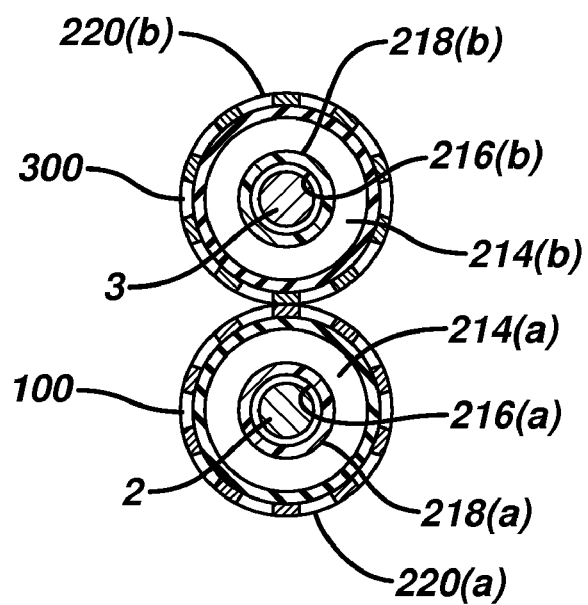
FIG. 7 is a cutaway view taken along line 7-7 of FIG. 5B.

As shown in FIGS. 5-7, the expansion members 220(*a*) and 220(*b*) are located at the distal ends of the distal portion 20 of the delivery system 10. As shown in FIG. 3, at least one marker band 234 may be located along the length the expansion members 220(*a*) and 220(*b*). Other markerbands can be located along delivery system 10. For example at least one band can be located proximal to the stent 100, one at the point where the expansion member 220 exits the stent 100, one distal to the stent 100, and one distal to the end of the stent 300. The expansion members include lumens through which wires 2, 3 pass exiting at distal tips 210(a)-(b). Distal tips 210(a)-(b) can assume a wide range of shapes such as being rounded or blunted. As shown in FIG. 4C, distal tips 210(a)-(b) are tapered to ease insertion of delivery system 10 into a vessel or conduit. Although shown having the same geometry, tips 210(a)-(b) can each have different geometries, dimensions, etc. and/or be made from different materials.

Figure 15:
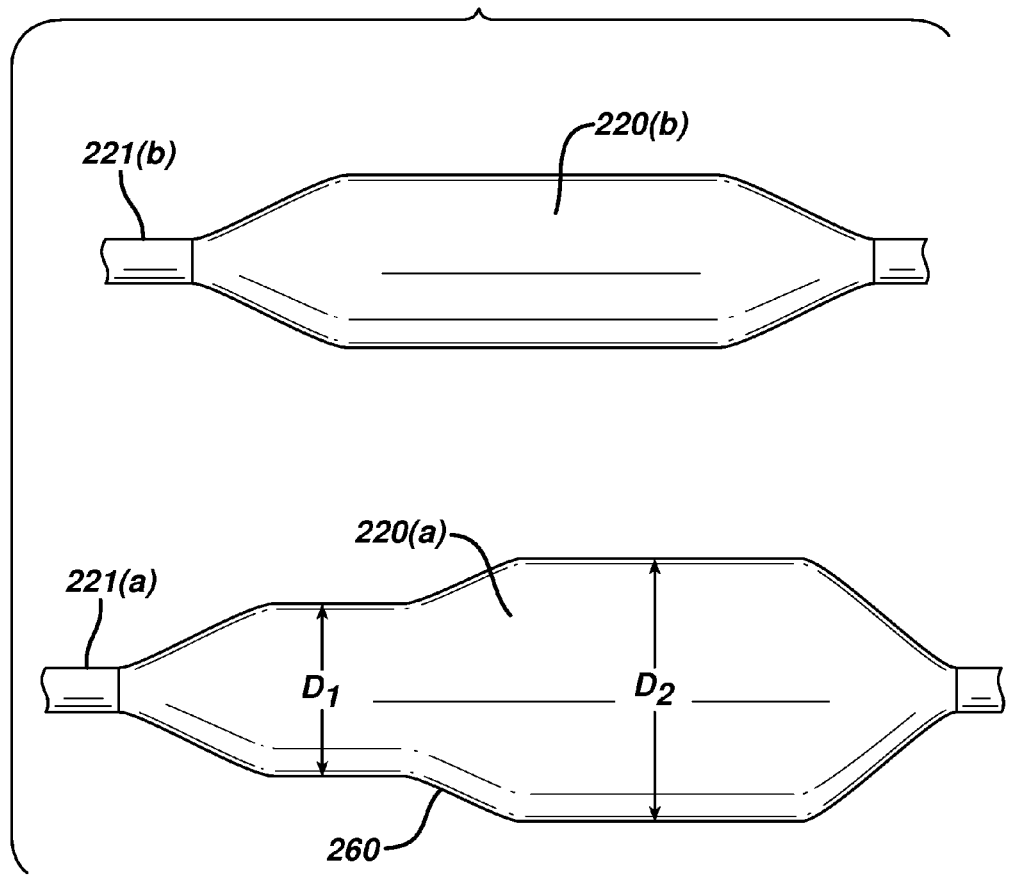
FIG. 15 is a side view showing an alternate embodiment for the expansion members of the delivery system.
Figure 16:
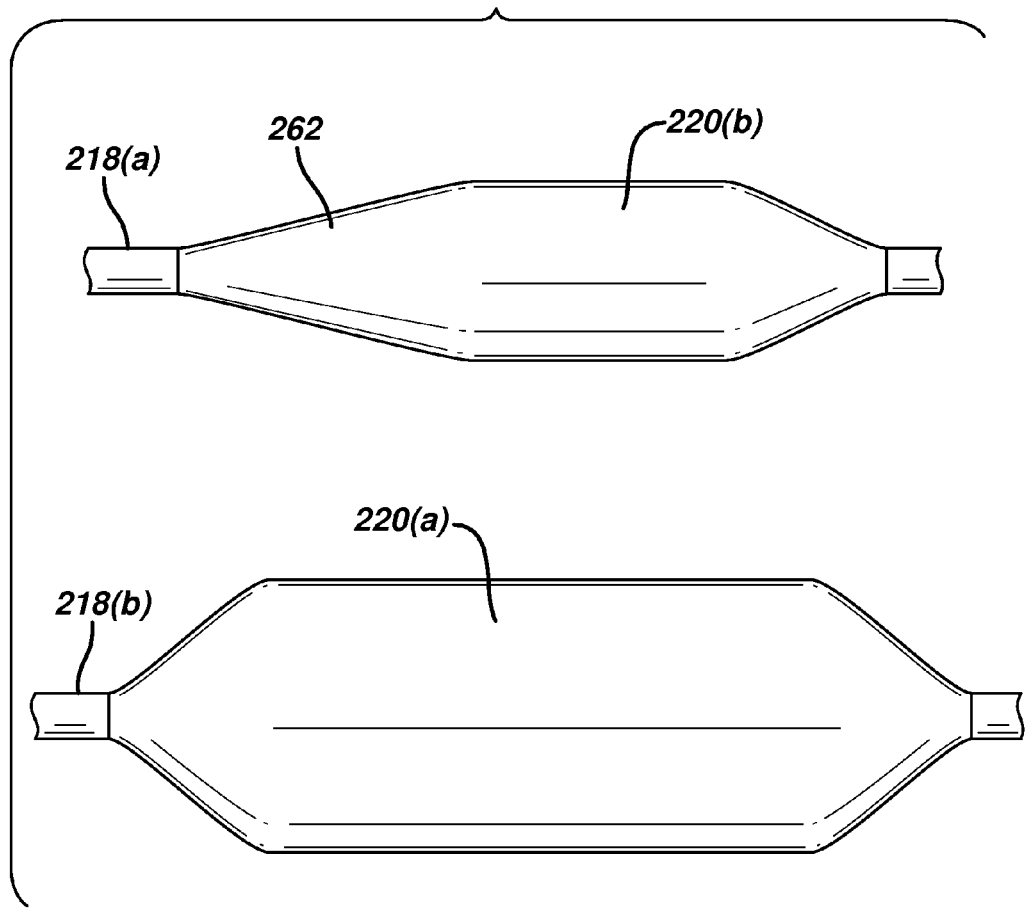
FIG. 16 is a side view showing an alternate embodiment for the expansion members of the delivery system.

In one embodiment of the invention, the expansion members 220(a) and 220(b) may comprise at least two balloons. A first balloon 220(b) is configured to extend into a side branch vessel and is generally shorter than a second balloon 220(a). Varying the length and the relative axial positions of the two balloons 220(a) and 220(b) optimizes cooperation between the balloons by minimizing overlap to match bifurcation anatomy. Alternatively, as shown in FIG. 15, at least one of the two balloons 220(a) and 220(b) has at least one step or elongated tapered section 260 that varies the diameter along the length of the balloon 220(a) such that one portion of the balloon has a smaller expansion diameter D1 and another portion has a larger expansion diameter D2. This allows for better matching of the bifurcation anatomy than if two similar length and shaped balloons are used. Yet another alternative is shown in FIG. 16 wherein one balloon has an elongated tapered section 262. The tapered section gradually varies the diameter of the balloon 220(b) to better fit the bifurcation geometry.

As shown in FIGS. 3 and 5B, First 100 and second 300 stent are mounted on the expansion members 220(a) and 220(b). If desired, additional stents, not shown in the figures, can be mounted on either expansion device 220(a)-(b) depending on the geometry of the vessel bifurcation. The first stent 100 is mounted on each of the members 220(a) and 220(b) such that the second member 220(a) extends through the length of the stent 100. The first stent 100 is modified as described above such that the first member 220(b) can extend through the components, i.e. struts 110, loop 112, bridges 116 or hoops 108 of the stent 100. A second stent 300 is mounted on the distal end of the first balloon 220(b). The second stent 300 is positioned just distal to where the first balloon 220(b) exits the first stent 100 and is generally shorter with an equal or smaller expansion diameter.

Figure 4A:
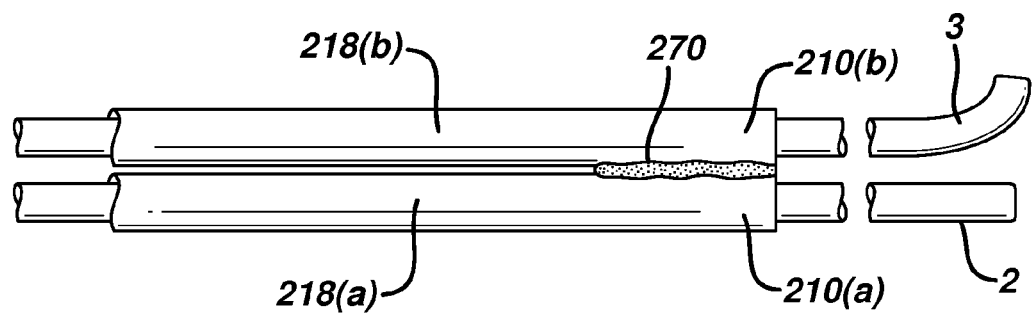
FIG. 4A is a side view showing the tips of the delivery system joined together.
Figure 4B:
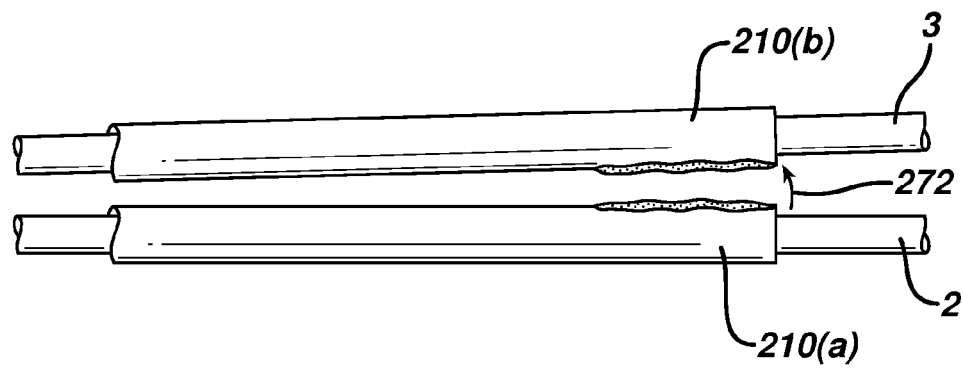
FIG. 4B is a side view showing the tips of the delivery system separated.
Figure 4C:
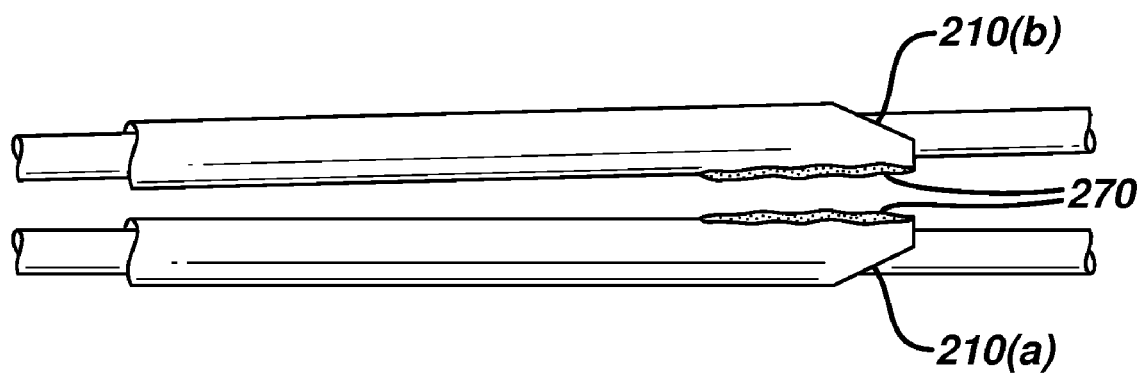
FIG. 4C is side view showing an alternate embodiment of the tips of the delivery system.

As shown in FIGS. 4A-C, a connection element 270 is positioned between the first stent 100 and the second stent 300, at the distal tips 210(a) and 210(b). This element releasably joins tips 210(a)-(b) together to prevent tip 210(b) from snagging the vessel while being delivered and aids in preventing wires 2 and 3 from wrapping due to torsional forces experienced as the expansion members 220(a)-(b) are advanced into the vessel bifurcation as is described in greater detail below. In particular, the tip joining element 270 releases in response to axial translation of system 10 and the resultant forces generated at the connection point allowing for controlled separation of the tips 210(a)-(b) only when the members are being positioned onto the carina or crotch of a bifurcation. In one embodiment of the invention, the element 270 comprises a mechanical connection such as a set of meshed teeth that act as a kind of zipper or a system of hooks and loops may be employed. In another embodiment of the invention, the tip joining element 270 may comprise a chemical bonding agent such as glue or a viscous polymer that will release at a given temperature, force and/or time. In yet another embodiment of the invention, the tips 210(a)-(b) are constructed from a polymeric material. Element 270 may comprise a thermal bond between the tips whereby each tip is heated to create conditions allowing the tips 210(a)-(b) to bond.

Figure 5E:
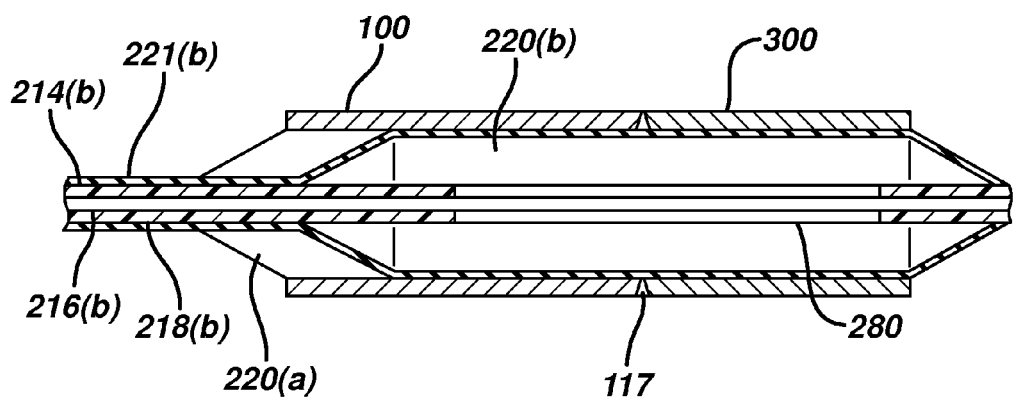
FIG. 5E is a top view taken along line 5E-5E of FIG. 5B.

As shown in FIG. 5E, a torque transition element 280 extends between the first stent 100 and the second stent 300. The transition element 280 prevents distal portions of stents 100 and 300 from wrapping due to torsional forces experienced as the expansion members 220(a)-(b) are advanced into the vessel bifurcation as is described in greater detail below. In addition, the torsional transition element 280 prevents the rotational "kinking" of the stents 100 and 300 can occur due to the rapid transition in torsional stiffness. The transition element 280 can be constructed by fabricating shafts 218(a) and/or 218(b) from a stiffer material and/or varying the geometry of the shafts 218(a) and/or 218(b). A braided section of shaft 218(a) and/or 218(b) can also be used for transition element 280.

Figure 8:
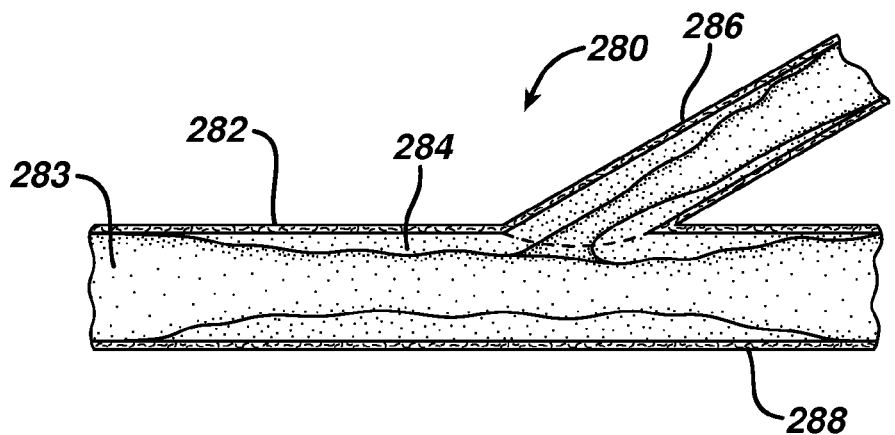
FIG. 8 is a side view of a vessel bifurcation.

The placement of stents 100 and 300 within a vessel bifurcation 280 is illustrated with reference to FIGS. 8-14. As shown in FIG. 8, a vessel bifurcation 280 comprises a main vessel 282 that branches into a side branch 286 and main branch 288 that are partially obstructed by plaque 284.

Figure 9:
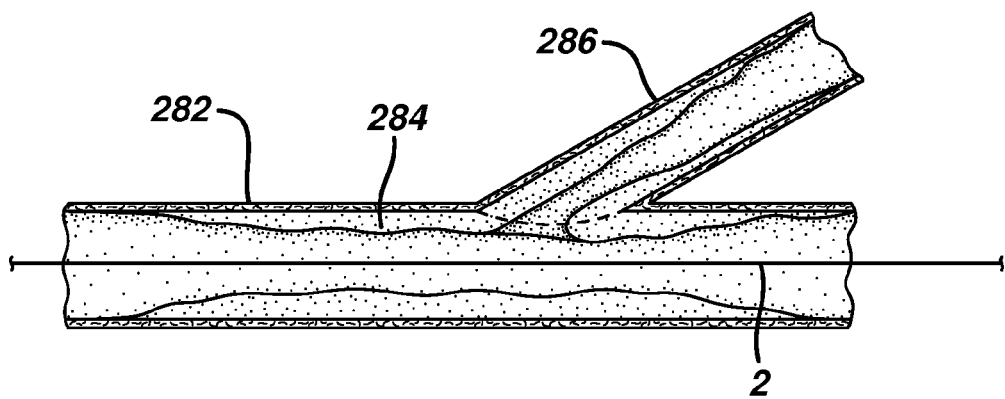
FIG. 9 is a side view showing a wire placed in the main branch of a vessel bifurcation.
Figure 10:
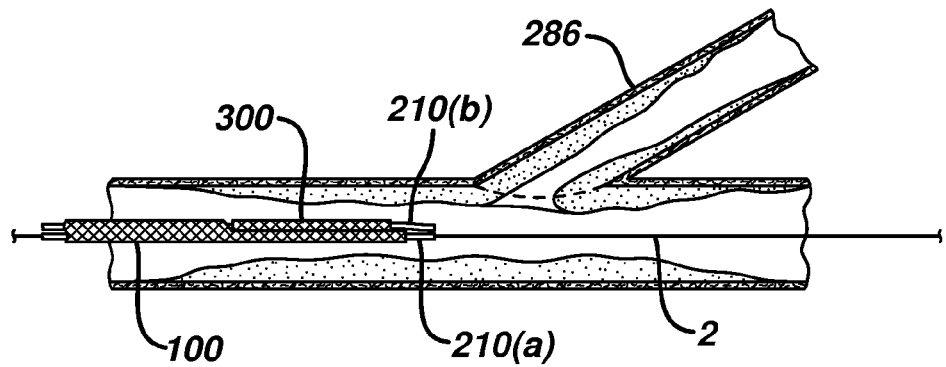
FIG. 10 is a side view showing the delivery system advanced along the wire just proximal to the vessel bifurcation.
Figure 11:
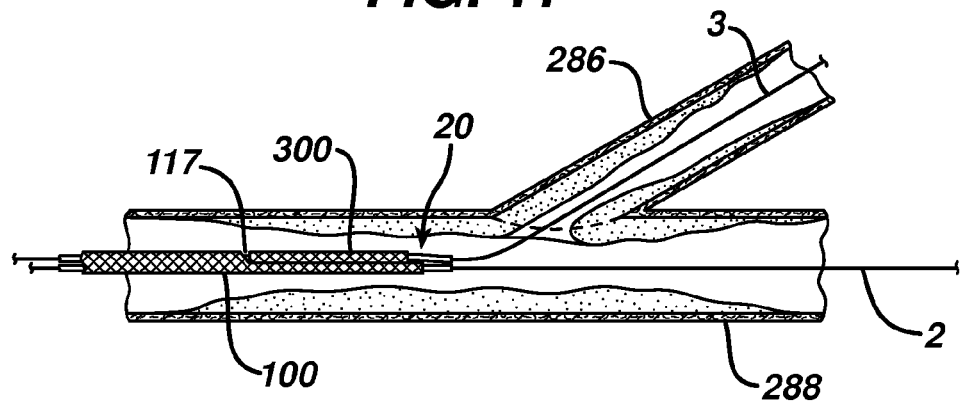
FIG. 11 is a side view showing a second wire advanced from the delivery system into a side branch vessel.
Figure 12:
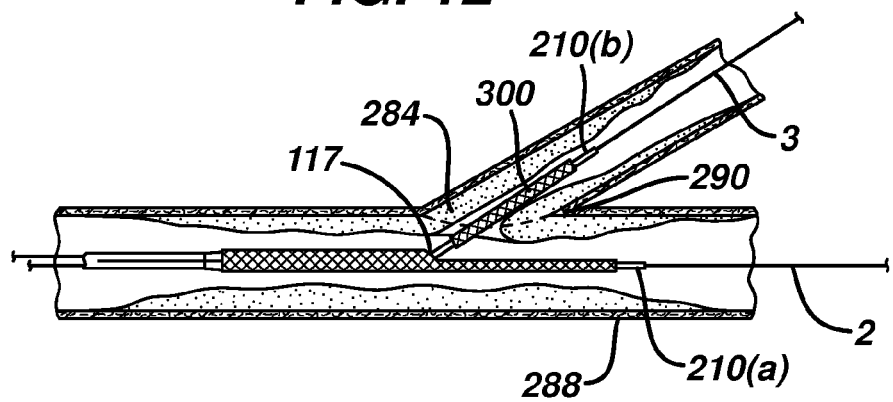
FIG. 12 is a side view showing the delivery system positioned such that the stents are placed in the branches of the vessel bifurcation.
Figure 13:
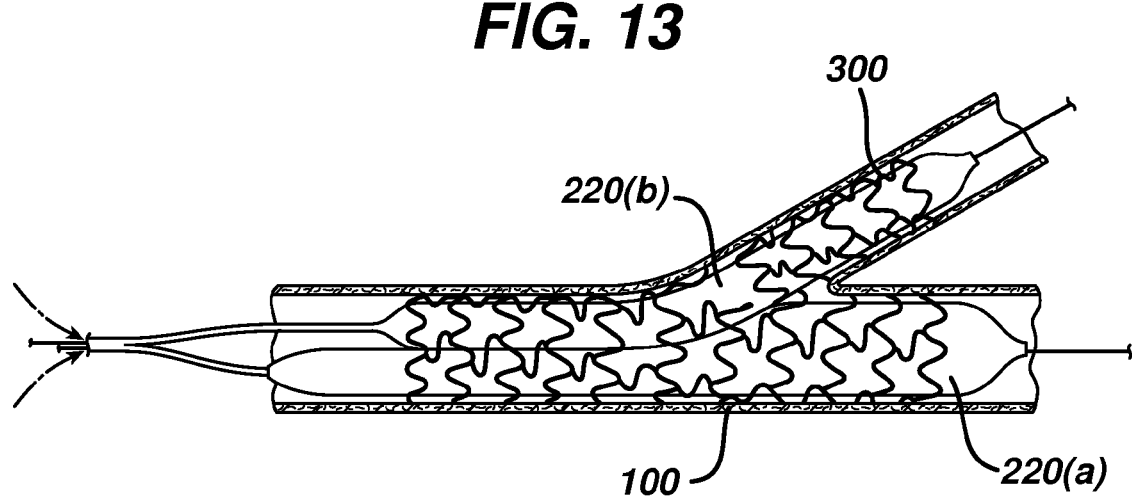
FIG. 13 is a side view showing the delivery system expanding the stents in the branches of the vessel bifurcation.
Figure 14:
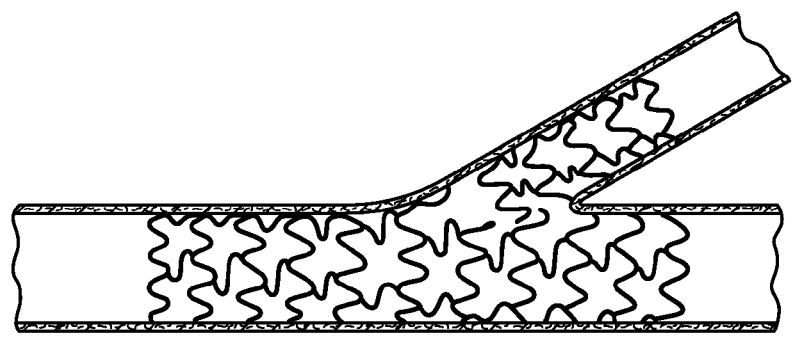
FIG. 14 is a side view showing the delivery system withdrawn from, and the stents emplaced in, the vessel bifurcation.

As shown in FIG. 9, a wire 2 is inserted into the lumen 283 of vessel 282 past the side branch 286. As shown in FIG. 10, stents 100 and 300, mounted on the expansion members 220(a)-(b) are positioned somewhere proximal to the ostium of side branch vessel 286 by sliding the system into place via wire 2 which is positioned within lumen 216(a). As shown in FIG. 11, a second wire 3 is then advanced through lumen 216(b) and into the lumen of the side branch vessel 286. As shown in FIG. 12, the distal ends 210(a)-(b) are advanced into the main branch 288 and side branch 286 which forces the tips 210(a)-(b), heretofore held together by releasable joining element 270, apart until the region 117 impinges, or nearly impinges, upon the crotch 290 of the bifurcation 280. Once positioned within bifurcation 280, members 220(a)-(b) are inflated through lumens 214(a)-(b) which are in communication with an inflation source. Stents 100 and 300 are then simultaneously or sequentially expanded by members 220 (a)-(b). Once in place, the members 220(a)-(b) are deflated and the system 10 removed from the vessel 282. Stents 100 and 300 are thereby implanted. The stents 100 and 300 maintain and improve the patency of vessel 282 and branches 286 and 288 of bifurcation 280.

Prior to insertion of the stents 100 and 300 the vessel 282 and bifurcation 280 can be pre-treated to partially clear the obstruction caused by plaque 284 using expansion members 220(a)-(b). This is accomplished in a manner similar to the method described above. Namely, wires 2 and 3 are placed in the side branch 286 and main branch 288. The expansion members 220(a)-(b) are tracked over the wires 2 and 3 until they are each in the side 286 and main 288 branch vessels. Once in position the members 220(a)-(b) are expanded to compress the plaque 284 and open the lumen 284 of the vessel 282 and the lumens of the side 286 and main 288 branch vessel. Thereafter, stents 100 and 300 can be placed using the method described above.

Although the present invention has been described above with respect to particular preferred embodiments, it will be apparent to those skilled in the art that numerous modifications and variations can be made to these designs without departing from the spirit or essential attributes of the present invention. Accordingly, reference should be made to the appended claims, rather than to the foregoing specification, as indicating the scope of the invention. The descriptions provided are for illustrative purposes and are not intended to limit the invention nor are they intended in any way to restrict the scope, field of use or constitute any manifest words of exclusion.

What is claimed is:

1. A method for placing at least two separate and detached devices in a vessel bifurcation comprising the steps of:
advancing a first wire into a main vessel past the vessel bifurcation and into a main branch of the vessel bifurcation;
advancing a system over the first wire that passes through a first lumen of the system to a point proximal to the vessel bifurcation, wherein the system has at least two separate and detached expansion members at its distal end with the at last two separate and detached devices mounted thereon such that at least one of the at least two devices is mounted on each of the at least two separate expansion members, each of the at least two expansion members having a distal tip, said tips being held together by a connector;
inducing a preferential bend along the system, the preferential bend having a predetermined fixed curved shape and being configured to automatically and freely rotate the system about the first wire relative to the vessel bifurcation to orient the system in a desired position;
once the system is advanced to the point proximal to the vessel bifurcation, advancing a second wire through a second lumen of the system into a side branch of the vessel bifurcation without first withdrawing the second wire through the second lumen;
advancing the system into the bifurcation along the first and second wires whereby the connector is released and the expansion members are advanced in parallel;
simultaneously positioning one of the at least two devices in the main vessel and the main branch of the vessel bifurcation, and the second of the at least two devices in the side branch vessel of the vessel bifurcation;
inflating the expansion members such that the devices are expanded to fill substantially the inner diameter of the main vessel and the side branch and main branch of the bifurcation;
deflating the expansion members;
withdrawing the second wire into the second lumen; and
removing the system along the first wire leaving the devices emplaced at the vessel bifurcation.

2. The method of claim 1 wherein one of the at least two expansion members are inflated sequentially.

3. The method of claim 1 wherein the at last two expansion members are inflated simultaneously.

4. The method of claim 1 wherein the system further comprises a first annular element having at least one lumen longitudinally disposed therein.

5. The method of claim 4 wherein the system further comprises at least two secondary annular elements each having at last one guide wire lumen in communication with the at least one lumen of the first annular element, the at least two secondary annular elements extending from the distal end of the first annular element.

6. The method of claim 5 wherein the at least two expansion members are mounted at the distal end of the at least two secondary annular elements.

7. The method of claim 6 wherein each expansion member is in fluid communication with at least one inflation source.

8. The method of claim 1 wherein one of the at least two expansion members passes through the length of the first of the at least two devices and the second of the at least two expansion members passes through at least a proximal portion of the first device and exits at a location between the proximal and a distal end of the first device.

9. The method of claim 1 wherein the second of the at least two devices is mounted on the second of the at least two expansion members such that the expansion member passes through the length of the second device.

10. The method of claim 1 wherein each of the at least two expansion members is affixed to a first annular element comprising a catheter.

11. The method of claim 1 wherein each of the at least two expansion members is affixed to a first annular element comprising a sheath.

12. The method of claim 1 further comprising at least two secondary annular elements affixed to the at least two expansion members which are substantially torsionally de-coupled allowing for rotation thereof.

13. The method of claim 1 wherein one of the at least two expansion members has a greater length.

14. The method of claim 1 wherein the at least two expansion members are substantially torsionally coupled at a location where the at least two expansion members separate.

15. The method of claim 1 wherein the at least two expansion members are substantially torsionally coupled at a location where the second expansion member exists the first device.

16. The method of claim 14 wherein increasing the bending stiffness of at least one of the expansion members at least in a direction orthogonal to a plane defined by the longitudinal axes of the expansion members torsionally couples the at least two expansion members.

17. The method of claim 15 wherein increasing the bending stiffness of at least one of the expansion members at least in a direction orthogonal to a plane defined by the longitudinal axes of the expansion members torsionally couples the at least two expansion members.

18. The method of claim 15, wherein the bending stiffness of a section of one of the expansion members is increased.

19. The method of claim 1 wherein the connection comprises a thermal bond.

20. The method of claim 19 wherein the tips are constructed from at least one polymeric material that has been heated to a pre-determined temperature to form a bond between the tips wherein the boned tips can be subsequently separated as the tips are advanced along the first and second divergent paths.

21. The method of claim 1 wherein the connection comprises a chemical composition.

22. The method of claim 21 wherein the chemical composition comprises an adhesive.

23. The method of claim 1 wherein the connection comprises a mechanical connection.

24. The method of claim 23 wherein the mechanical connection comprises a set of teeth mounted on each tip such that the teeth are in mating contact to thereby hold the tips together.

25. The method of claim 23 wherein the mechanical connection comprises a set of loops mounted on a first of the tips and a set of hooks mounted on a second of the tips said loops and hooks being brought into contact so as to engage and hold the tips together.

26. The method of claim 1 wherein at least one of the distal ends of the distal tips is beveled.

27. The method of claim 1 wherein a third device is mounted on one of the at least two expansion members adjacent to the second of the at least two devices.

28. The method of claim 1 wherein at least one of the at least two devices includes at least one therapeutic agent.

29. The method of claim 28, wherein the at least one therapeutic agent comprises anti-proliferative agents.

30. The method of claim 28, wherein the at least one therapeutic agent comprises anti-thrombogenic agents.

31. The method of claim 28, wherein the at least one therapeutic agent comprises anti-restenotic agents.

32. The method of claim 28, wherein the at least one therapeutic agent comprises anti-infective agents.

33. The method of claim 28, wherein the at least one therapeutic agent comprises anti-viral agents.

34. The method of claim 28, wherein the at least one therapeutic agent comprises anti-bacterial agents.

35. The method of claim 28, wherein the at least one therapeutic agent comprises anti-fungal agents.

36. The method of claim 28, wherein the at least one therapeutic agent comprises anti-inflammatory agents.

37. The method of claim 28, wherein the at least one therapeutic agent comprises cytostatic agents.

38. The method of claim 28, wherein the at least one therapeutic agent comprises cytotoxic agents.

39. The method of claim 28, wherein the at least one therapeutic agent comprises immunosuppressive agents.

40. The method of claim 28, wherein the at least one therapeutic agent comprises anti-microbial agents.

41. The method of claim 28, wherein the at least one therapeutic agent comprises anti-calcification agents.

42. The method of claim 28, wherein the at least one therapeutic agent comprises anti-encrustation agents.

43. The method of claim 28, wherein the at least one therapeutic agent comprises statins.

44. The method of claim 28, wherein the at least one therapeutic agent comprises hormones.

45. The method of claim 28, wherein the at least one therapeutic agent comprises anti-cancer agents.

46. The method of claim 28, wherein the at least one therapeutic agent comprises anti-coagulants.

47. The method of claim 28, wherein the at least one therapeutic agent comprises anti-migratory agents.

48. The method of claim 28, wherein the at least one therapeutic agent comprises tissue growth promoting agents.

49. The method of claim 1, wherein at least one of the at least two expansion members has a first section having a first diameter and a second section having a second diameter greater than the first diameter and an elongated tapered section interspersed between the first and second section.

50. The method of claim 1, wherein the at least one of the at least two expansion members has a first elongated tapered section terminating at a second section.

51. The method of claim 1, wherein at last one of the at least two devices comprises a stent.

* * * * *